(12) United States Patent
Maier et al.

(10) Patent No.: US 8,104,957 B2
(45) Date of Patent: Jan. 31, 2012

(54) CALIBRATING A C-ARM X-RAY APPARATUS

(75) Inventors: Christian Maier, München (DE); Jörg Uhde, München (DE)

(73) Assignee: Brainlab AG, Feldkirchen (DE)

( * ) Notice: Subject to any disclaimer, the term of this patent is extended or adjusted under 35 U.S.C. 154(b) by 134 days.

(21) Appl. No.: 12/397,390

(22) Filed: Mar. 4, 2009

(65) Prior Publication Data

US 2009/0226070 A1 Sep. 10, 2009

Related U.S. Application Data

(60) Provisional application No. 61/035,511, filed on Mar. 11, 2008.

(30) Foreign Application Priority Data

Mar. 4, 2008 (EP) .................................. 08152242

(51) Int. Cl.
*G01D 18/00* (2006.01)
*A61B 6/08* (2006.01)

(52) U.S. Cl. ................... 378/207; 378/98.3; 378/205

(58) Field of Classification Search ............... 378/41, 378/62, 63, 91, 98, 98.2, 98.3, 98.5, 98.8, 378/98.12, 205, 210, 207
See application file for complete search history.

(56) References Cited

U.S. PATENT DOCUMENTS

| | | | | |
|---|---|---|---|---|
| 5,247,555 | A * | 9/1993 | Moore et al. | 378/4 |
| 5,841,148 | A * | 11/1998 | Some et al. | 250/584 |
| 6,379,041 | B1 * | 4/2002 | Schuetz et al. | 378/205 |
| 6,491,429 | B1 * | 12/2002 | Suhm | 378/205 |
| 6,516,046 | B1 * | 2/2003 | Frohlich et al. | 378/65 |
| 6,535,574 | B1 * | 3/2003 | Collins et al. | 378/65 |
| 6,697,664 | B2 * | 2/2004 | Kienzle, III et al. | 600/427 |
| 6,739,752 | B2 | 5/2004 | Sabczynski et al. | |

(Continued)

FOREIGN PATENT DOCUMENTS

WO 00/47103 8/2000

(Continued)

*Primary Examiner* — Anastasia Midkiff
(74) *Attorney, Agent, or Firm* — Renner, Otto, Boisselle & Sklar, LLP

(57) ABSTRACT

The invention relates to a method for calibrating a C-arm x-ray apparatus, comprising the following steps:
a) the C-arm x-ray apparatus is moved to an initial position, in particular to an anterior-posterior position;
b) a calibration image is produced;
c) the position of the centre of projection in the radiation source of the C-arm x-ray apparatus is determined from the information of the calibration image and stored together with associated values for the orbital angle and the polar angle of the arm of the C-arm x-ray apparatus;
d) the arm is moved to a number of calibration positions in a range of orbital angles and polar angles, and the relative position of the radiation source and the image intensifier of the C-arm x-ray apparatus is directly measured for each calibration position;
e) the change in the position of the radiation source relative to the image intensifier of the C-arm x-ray apparatus is measured for each calibration position;
f) the position of the centre of projection which applies to each calibration position is ascertained from:
the position of the centre of projection, as determined in Step c); and from
the change in the position of the radiation source relative to the image intensifier; and
g) the position of the centre of projection is retrievably stored for each calibration position, i.e. for the respective orbital angle and the respective polar angle.

17 Claims, 1 Drawing Sheet

U.S. PATENT DOCUMENTS

| | | | |
|---|---|---|---|
| 6,771,734 B2 * | 8/2004 | Hebecker et al. | 378/8 |
| 6,814,489 B2 * | 11/2004 | Jensen et al. | 378/197 |
| 6,851,855 B2 | 2/2005 | Mitschke et al. | |
| 6,932,506 B2 | 8/2005 | Mitschke et al. | |
| 7,251,522 B2 | 7/2007 | Essenreiter et al. | |
| 7,505,559 B2 * | 3/2009 | Kuduvalli | 378/65 |
| 7,519,415 B2 * | 4/2009 | Mitschke et al. | 600/424 |
| 2001/0053204 A1 * | 12/2001 | Navab et al. | 378/205 |
| 2005/0207529 A1 * | 9/2005 | Boese et al. | 378/41 |
| 2009/0074136 A1 * | 3/2009 | Kamegawa | 378/20 |

FOREIGN PATENT DOCUMENTS

| | | |
|---|---|---|
| WO | 2004/052205 | 6/2004 |

\* cited by examiner

CALIBRATING A C-ARM X-RAY APPARATUS

RELATED APPLICATION DATA

This application claims the priority of U.S. Provisional Application No. 61/035,511, filed on Mar. 11, 2008, which is hereby incorporated in its entirety by reference.

FIELD OF THE INVENTION

The invention relates to calibrating a C-arm x-ray apparatus. It relates in particular to a method for such a calibration and to a method for determining the relative position of the centre of projection and the image intensifier of a C-arm x-ray apparatus with the aid of a calibration.

BACKGROUND OF THE INVENTION

In fluoroscopy-assisted, image-guided surgery, it is necessary to register each C-arm image before it can be used for navigation purposes. To this end, a device (registration kit) which can be localized in a medical tracking system is conventionally attached to the image intensifier of the C-arm. The registration kit has a pattern of radio-opaque markers which are imaged on the C-arm image when the image is produced. The opaque markers have to be arranged in such a way that they do not completely lie in one plane, which means that they have to be provided in a three-dimensional distribution. The relative position of the imaged markers can then be used to determine the centre of projection of the image produced. To this end, the tracked device—i.e. the registration kit—has to have a spatial extension and remain on the C-arm for each image produced, because the centre of projection has a different position relative to the image intensifier for each image-generating direction. This is due to the fact that the C-arm only has a finite rigidity and is subject to different deformations in different positions.

U.S. Pat. Nos. 6,851,855 B2, 6,932,506 B2 and 7,251,522 B2 describe calibration processes for a C-arm, wherein it is always necessary during calibration to always also produce respective calibration images for each image-generating direction. In other words: at each angle for which the C-arm is to be calibrated during calibration, it is also necessary to produce a calibration image in order to ascertain the respective centre of projection.

SUMMARY OF THE INVENTION

It is the object of the present invention to configure the calibration of a C-arm x-ray apparatus to be simpler and in particular also less elaborate and/or quicker. This object is solved in accordance with the invention by a method for calibrating a C-arm x-ray apparatus, comprising the following steps:
a) the C-arm x-ray apparatus is moved to an initial position, in particular to an anterior-posterior position;
b) a calibration image is produced;
c) the position of the centre of projection in the radiation source of the C-arm x-ray apparatus is determined from the information of the calibration image and stored together with associated values for the orbital angle and the polar angle of the arm of the C-arm x-ray apparatus;
d) the arm is moved to a number of calibration positions in a range of orbital angles and polar angles, and the relative position of the radiation source and the image intensifier of the C-arm x-ray apparatus is directly measured for each calibration position;
e) the change in the position of the radiation source relative to the image intensifier of the C-arm x-ray apparatus is measured for each calibration position;
f) the position of the centre of projection which applies to each calibration position is ascertained from:
the position of the centre of projection, as determined in Step c); and from
the change in the position of the radiation source relative to the image intensifier; and
g) the position of the centre of projection is retrievably stored for each calibration position, i.e. for the respective orbital angle and the respective polar angle.

The sub-claims define preferred embodiments of the invention.

Thus, unlike the prior art, a calibration image is not "shot" (with the registration kit attached) every time, i.e. in each calibration position, in the method in accordance with the invention, but rather this process only has to be performed once, in order to establish where the centre of projection lies relative to the radiation source (the component comprising the x-ray tube at one end of the C-arm) or relative to a tracking reference on the radiation source. The invention is based on the realization that the centre of projection itself will not change in its relative position in the radiation source and/or relative to a reference on the radiation source, irrespective of the position which the C-arm is situated in. This knowledge then enables the position of the centre of projection to be deduced directly from the position of the radiation source or the reference fastened to it. If the position of the image intensifier is then also shown, the relative position of the radiation source and the image intensifier can be established, without having to generate an image especially for each calibration angle. In other words: Steps b) and c) as cited above provide absolute coordinates for the centre of projection (preferably in the image intensifier coordinate system), and Step d) then provides the relative changes to this position which have to be added to the absolute coordinates in order to obtain the new absolute position of the centre of projection.

The invention thus includes a method for storing information concerning the centre of projection of an image for each possible image-producing direction in the navigation system. This information is obtained by performing a calibration procedure which enables the centre of projection of the image relative to the image intensifier of the C-arm to be determined for every possible image-producing direction. The coordinates of the centre of projection of the image are stored for each image-producing direction, on the navigation system which is used for the fluoroscopic navigation and/or fluoroscopically guided treatment. While the C-arm is being intra-operatively used, the current image-producing direction is determined, and the respective centre of projection of the image can then be located from the stored data.

Using the present invention, it is no longer necessary to fasten a device, which enables the centre of projection of each image recorded to be determined, to the image intensifier in each calibration position. Since such a device has to have a three-dimensional extension, it usually takes up a certain amount of space between the C-arm radiation source and the image intensifier, and thus makes the C-arm more awkward and difficult to operate. Using the method in accordance with the invention, this can be avoided. Also, the centers of projection for each image-detecting direction are determined beforehand in accordance with the invention, such that the intra-operative computational time is reduced. The calibration is also very low in radiation, because only a single fluoroscopic image has to be produced.

In one embodiment of the present invention, at least one of the components of the C-arm x-ray apparatus is spatially localized and/or tracked by a medical tracking system, wherein the tracking data is in particular processed with the aid of a medical navigation system. The navigation system can also process and prepare the other data which is generated or input during calibration as a whole.

As already mentioned above, the position of the centre of projection can be determined in Step c) relative to a coordinate system which is fixed relative to the image intensifier.

When producing the calibration image, it is possible to attach a registration kit to the image intensifier of the apparatus, said registration kit comprising an imaging pattern which is imaged in the calibration image, from which the centre of projection can be ascertained, specifically in a coordinate system of the registration kit.

In accordance with an embodiment variant, the registration kit is tracked from without by a medical tracking system or is attached to the trackable image intensifier of the C-arm x-ray apparatus in a known and/or predetermined position, such that the centre of projection can be ascertained in the coordinate system which is fixed relative to the image intensifier (internally). The radiation source can likewise be tracked from without by a medical tracking system, and this has the result that the centre of projection can also be ascertained in the coordinate system which is fixed relative to the radiation source, and/or a corresponding transformation is possible.

The registration kit can be removed from the C-arm, i.e. from the image intensifier, before the step of directly measuring the relative position.

In accordance with the invention, it is possible for the relative position of the radiation source and the image intensifier of the C-arm x-ray apparatus to be directly measured from without by tracking references attached to them, using the tracking system.

The respective orbital angles and the respective polar angles can be measured in different ways, for example by:
i)—directly determining the position of the arm with the aid of the tracking references of the radiation source and/or image intensifier; and
—directly determining the position of the C-arm holder by means of a tracking reference attached to it;
or by
ii)—directly determining the position of the C-arm holder by means of a tracking reference attached to it; and
—using electr(on)ic, electromechanical or mechanical longitudinal movement sensors and/or angular sensors and/or tappers for the angles.

In one embodiment of the invention, the change in the position of the radiation source relative to the position of the radiation source in the initial position is likewise again measured by the tracking system.

In accordance with another aspect, the invention relates to a method for determining the relative position of the centre of projection and image intensifier of a C-arm x-ray apparatus, wherein the relative position is determined from a calibration position which is determined for corresponding orbital angles and polar angles, after a calibration in accordance with one of the methods such as have been illustrated above in different embodiments.

BRIEF DESCRIPTION OF THE DRAWINGS

The invention will now be illustrated in more detail on the basis of an example embodiment and with the aid of enclosed drawings. It can include any of the features described here, individually and in any expedient combination. The one enclosed figure, FIG. 1, schematically shows a C-arm x-ray apparatus in its tracking environment.

DETAILED DESCRIPTION

Figure 1:
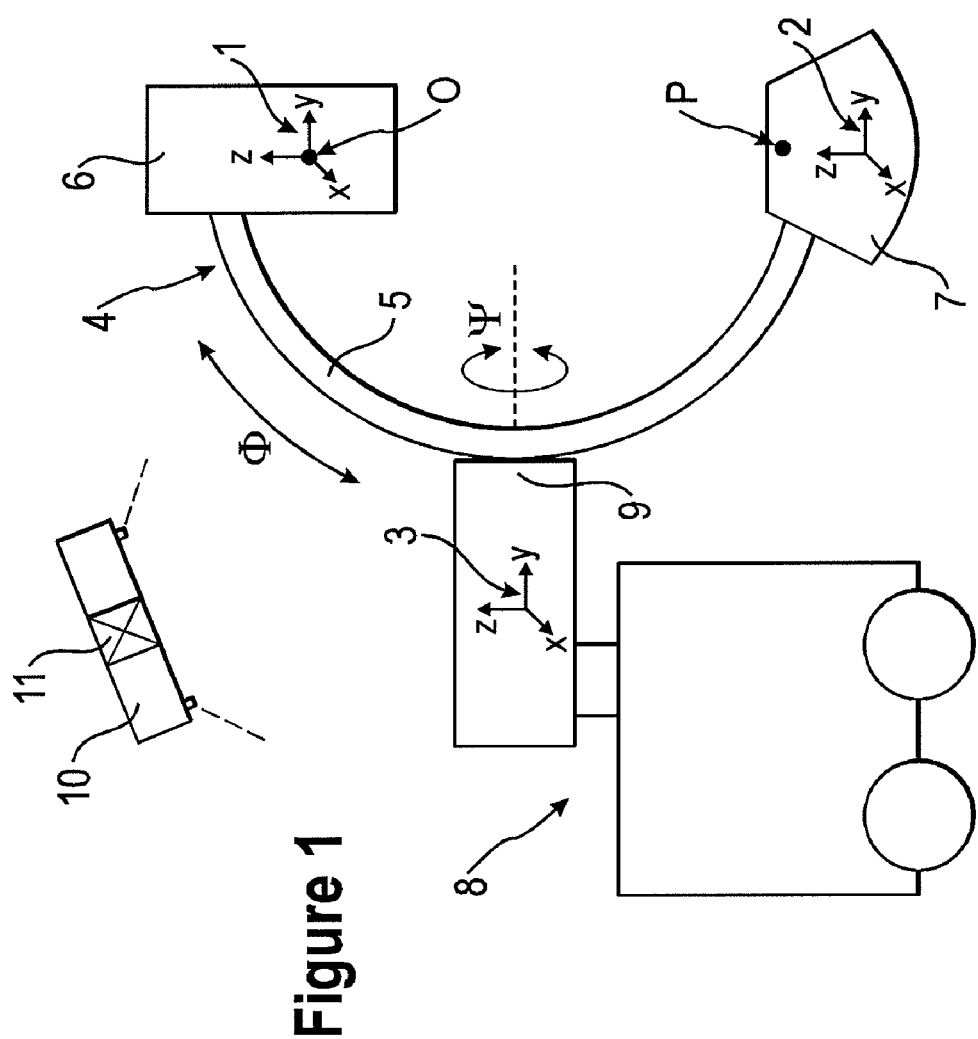

The C-arm x-ray apparatus 4 shown in FIG. 1 comprises a carriage 8 (C-arm holder) which has a coordinate system 3 which is fixed relative to the carriage. The arm 5 of the C-arm x-ray apparatus 4 is fastened to the carriage 8, such that it can be rotated in the polar direction $\psi$ and shifted along the arm in the angular direction $\varphi$ (orbital direction). On the lower side, the radiation source 7 comprising the coordinate system 2 which is fixed relative to the radiation source is attached to the arm 5. In this case, the component itself—which will include an x-ray tube (not individually shown)—represents the radiation source 7. The centre of projection is marked by the letter P and lies somewhere in or on the radiation source. The centre of projection is dependent on the design of the radiation source and its elements, and its position can only be determined from this design with difficulty. It is better to determine the centre of projection by means of a registration kit, as already described above.

The image intensifier 6, comprising the coordinate system 1 (centre point O) which is fixed relative to the image intensifier, is situated at the upper end of the arm 5.

The coordinate systems 1, 2 and 3 can also be conceived as tracking references, for example as reference stars comprising active or passive markers for the tracking unit and/or tracking system 10 which is only schematically shown and to which the navigation system 11 is connected. The tracking system and navigation system 10, 11 are medical systems such as are conventionally used in image-guided surgery.

Described in brief, calibration of the C-arm 4 is based on the following principles: firstly, the position of the centre of projection P of the image (coordinate system 2) with respect to the position of the image intensifier (coordinate system 1) has to be known. Secondly, the position of the image intensifier (coordinate system 1) with respect to the carriage 8 (coordinate system 3) has to be known for a particular image-generating direction. This information concerning the image-generating direction and the respective centre of projection of the image can be stored on the navigation system and automatically retrieved while intra-operatively using the C-arm 4. This means that the image-generating direction has to be determined first, and it is then possible to retrieve, from the stored calibration data, the centre of projection of the image which is associated with this image-generating direction.

Expressed in very general terms, the C-arm calibration in accordance with the invention requires the following four components:

Firstly, a device which is attached to the C-arm radiation source and allows a coordinate system to be established at the radiation source (coordinate system 2). The centre of projection P of the image has fixed but initially unknown coordinates in this coordinate system. One example of such a device would be a tracking reference (optical, electromagnetic, etc.) which is attached to the cover of the radiation source.

A second element is a device for determining the coordinates of the centre of projection P of the image in the coordinate system 2, and to this end, a conventional tracked registration kit can for example be attached to the image intensifier.

A third element is a device for determining the position of the image intensifier (coordinate system 1) relative to the C-arm holder or the carriage 8 (coordinate system 3), thus ascertaining the values of the orbital angles $\varphi$ and the polar angles $\psi$. To this end, tracking markers can again be attached to the image intensifier and the C-arm holder (carriage) 8, or electric, electromechanical or mechanical sensors are used which measure or read the orbital and polar movements relative to the guide 9 on the carriage 8.

Lastly, a device is also required for transforming the coordinates of the coordinate system 2 into coordinates of the coordinate system 1, and to this end, it is again possible to attach tracking references to the radiation source and the image intensifier, wherein these are only required during calibration. The computational tasks for the transformations can be performed in the navigation system.

Given these preconditions, the sequence of a calibration in accordance with the invention can then be described in accordance with an example embodiment, as follows:

The C-arm 4 is firstly moved to a particular specified image-generating direction, for example an anterior-posterior position (vertical alignment of the arm 5). An image is then produced using a conventional registration kit (not shown) which is attached to the image intensifier. The navigation system 11 calculates the coordinates of the centre of projection P with respect to the internal coordinates of the registration kit. These coordinates are then transformed into coordinates of the coordinate system of the image intensifier (coordinate system 1) and into coordinates of the coordinate system of the radiation source 7 (coordinate system 2). The coordinates of the centre of projection of the image for this specific (anterior-posterior) image-generating direction are thus known in the coordinate system 1 and in the coordinate system 2. Lastly, these coordinates for $\phi$ (orbital angle) and $\psi$ (polar angle) for the specific image-generating direction are stored in the navigation system.

The registration kit is then removed, while the tracking references on the image intensifier 6, the radiation source 7 and the carriage 8 still remain in place.

The arm 5 is then moved through its range of possible movement for the orbital and polar movement, and the tracking system 10 shows the positions of the three tracking references (which establish the coordinate systems 1, 2 and 3) during the whole of this calibration procedure, i.e. the values for $\phi$ and $\psi$ are respectively recorded together with the relative position of the radiation source and the image intensifier. The positional coordinates of the radiation source relative to the image intensifier will deviate from the values which were obtained when the initial image was generated, and these deviations can be added to the coordinates which were initially obtained for the centre of projection of the image (when the image was generated). New coordinates for the centre of projection of the image are thus obtained. It is important for the C-arm as a whole to be in mechanical equilibrium of the arm 5 for each position recorded, such that residual oscillations of the more remote parts do not impair the accuracy of the calibration.

Once the calibration steps described have been performed, the devices for determining the relative position of the radiation source and the image intensifier, i.e. for example the tracking references, can be removed.

While being intra-operatively used, the navigation system then automatically determines the relative position of the image intensifier and the C-arm carriage (the values for $\phi$ and $\psi$) and retrieves the corresponding position of the centre of projection of the image relative to the image intensifier, as determined by the calibration process.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments.

Although the invention has been shown and described with respect to one or more particular preferred embodiments, it is clear that equivalent amendments or modifications will occur to the person skilled in the art when reading and interpreting the text and enclosed drawings of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment or embodiments illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A method for calibrating a C-arm x-ray apparatus, said C-arm x-ray apparatus including an arm having a radiation source and an image intensifier, the method comprising the following steps:
   a) moving the C-arm x-ray apparatus to an initial position;
   b) acquiring a calibration image, wherein values for an orbital angle and polar angle of the arm of the C-arm apparatus during acquisition of the calibration image are stored;
   c) determining a position of the center of projection in the radiation source based on information obtained from the calibration image and the corresponding values for the orbital angle and the polar angle of the arm of the C-arm x-ray apparatus;
   d) moving the arm to a number of calibration positions in a range of orbital angles and polar angles, and directly measuring a relative position of the radiation source and the image intensifier of the C-arm x-ray apparatus for each calibration position;
   e) measuring a change in the position of the radiation source relative to the image intensifier of the C-arm x-ray apparatus for each calibration position;

f) ascertaining the position of the center of projection corresponding to each calibration position from:
the position of the center of projection, as determined in Step c); and from
the change in the position of the radiation source relative to the image intensifier; and
g) retrievably storing the position of the center of projection for each calibration position.

2. The method according to claim 1, wherein the initial position is an anterior-posterior position.

3. The method according to claim 1, further comprising using a medical tracking system to spatially localize and/or track at least one of the components of the C-arm x-ray apparatus.

4. The method according to claim 3, further comprising using a medical navigation system to process the tracking data.

5. The method according to claim 1, wherein determining the position of the center of projection includes determining the position relative to a coordinate system that is fixed relative to the image intensifier.

6. The method according to claim 1, wherein acquiring the calibration image includes attaching a registration kit to the image intensifier, said registration kit comprising an imaging pattern that is imaged in the calibration image, and ascertaining the center of projection based on said calibration image.

7. The method according to claim 6, wherein ascertaining the position of the center of projection includes ascertaining the center of projection in a coordinate system of the registration kit.

8. The method according to claim 6, wherein the registration kit is trackable by a medical tracking system or is attached to the trackable image intensifier of the C-arm x-ray apparatus in a known and/or predetermined position, and ascertaining the center of projection in the coordinate system that is fixed relative to the image intensifier.

9. The method according to claim 1, further comprising using a medical tracking system to track the radiation source, and ascertaining the center of projection in the coordinate system that is fixed relative to the radiation source.

10. A method for calibrating a C-arm x-ray apparatus, said C-arm x-ray apparatus including an arm having a radiation source and an image intensifier, the method comprising the following steps:
a) moving the C-arm x-ray apparatus to an initial position;
b) acquiring a calibration image using a registration kit comprising an imaging pattern that is imaged in the calibration image, wherein values for an orbital angle and polar angle of the arm of the C-arm apparatus during acquisition of the calibration image are stored;
c) determining a position of the center of projection in the radiation source based on information obtained from the calibration image and the corresponding values for the orbital angle and the polar angle of the arm of the C-arm x-ray apparatus;
d) moving the arm to a number of calibration positions in a range of orbital angles and polar angles, and directly measuring a relative position of the radiation source and the image intensifier of the C-arm x-ray apparatus for each calibration position;
e) measuring a change in the position of the radiation source relative to the image intensifier of the C-arm x-ray apparatus for each calibration position;
f) ascertaining the position of the center of projection corresponding to each calibration position from:
the position of the center of projection, as determined in Step c); and from
the change in the position of the radiation source relative to the image intensifier; and
retrievably storing the position of the center of projection for each calibration position,
wherein the registration kit is removed before performing Step d).

11. The method according to claim 3, wherein Step d) further includes using the tracking system to track tracking references attached to the radiation source and image intensifier, and based on tracked positions of the tracking references directly measuring the relative position of the radiation source and the image intensifier.

12. The method according to claim 3, further comprising measuring the respective orbital angles and the respective polar angles by:
i) —directly determining the position of the arm with the aid of the tracking reference of the radiation source and/or the tracking reference of the image intensifier; and
—directly determining the position of the C-arm holder from a tracking reference attached to the C-arm holder;
or by
ii) —directly determining the position of the C-arm holder from a tracking reference attached to the C-arm holder; and
—using electr(on)ic, electromechanical or mechanical longitudinal movement sensors and/or angular sensors and/or tappers to determine the angles.

13. The method according to claim 3, wherein measuring the change in the position includes using the tracking system to measure the change in position.

14. A method for determining the relative position of the center of projection and image intensifier of a C-arm x-ray apparatus, wherein the relative position is determined from a calibration position that is determined for corresponding orbital angles and polar angles, after a calibration in accordance with claim 1.

15. A computer program stored on a non-transitory machine-readable medium for calibrating a C-arm x-ray apparatus, said C-arm x-ray apparatus including an arm having a radiation source and an image intensifier, the program comprising:
code for moving the C-arm x-ray apparatus to an initial position;
code for acquiring a calibration image, and for storing values for an orbital angle and polar angle of the arm of the C-arm apparatus during acquisition of the calibration image;
code for determining a position of the center of projection in the radiation source based on information obtained from the calibration image and the corresponding values for the orbital angle and the polar angle of the arm of the C-arm x-ray apparatus;
code for moving the arm to a number of calibration positions in a range of orbital angles and polar angles, and directly measuring a relative position of the radiation source and the image intensifier of the C-arm x-ray apparatus for each calibration position;
code for measuring a change in the position of the radiation source relative to the image intensifier of the C-arm x-ray apparatus for each calibration position;
code for ascertaining the position of the center of projection which applies to each calibration position from:
the position of the center of projection, as determined in Step c); and from the change in the position of the radiation source relative to the image intensifier; and code for retrievably storing the position of the center of projection for each calibration position.

16. The computer program according to claim 15, wherein the initial position is an anterior-posterior position.

17. The method according to claim 1, wherein acquiring the calibration image comprises acquiring an X-ray calibration image using a registration kit comprising an imaging pattern that is imaged in the calibration image.

* * * * *